(12) United States Patent
Dardik

(10) Patent No.: US 6,702,720 B2
(45) Date of Patent: Mar. 9, 2004

(54) SYSTEMS AND METHODS FOR BREATHING EXERCISE REGIMENS TO PROMOTE ISCHEMIC PRECONDITIONING

(75) Inventor: Irving I. Dardik, Califon, NJ (US)

(73) Assignee: Lifewaves International, Inc., Califon, NJ (US)

(*) Notice: Subject to any disclaimer, the term of this patent is extended or adjusted under 35 U.S.C. 154(b) by 450 days.

(21) Appl. No.: 09/841,218

(22) Filed: Apr. 24, 2001

(65) Prior Publication Data

US 2002/0155924 A1 Oct. 24, 2002

(51) Int. Cl.$^7$ ............................................. A63B 23/18
(52) U.S. Cl. ............................................. 482/13; 600/538
(58) Field of Search ............................. 482/13; 600/529, 600/533, 538; 128/200.24, 204.18

(56) References Cited

U.S. PATENT DOCUMENTS 4,281,663 A   8/1981   Pringle ........................ 128/689
4,981,295 A * 1/1991   Belman et al. ................ 482/13
5,921,891 A   7/1999   Browne .......................... 482/8
6,165,105 A * 12/2000  Boutellier et al. ............ 482/13

FOREIGN PATENT DOCUMENTS

| EP | 255621 | 2/1988 |
| EP | 922434 | 6/1999 |
| EP | 956819 | 11/1999 |

* cited by examiner

Primary Examiner—Glenn E. Richman
(74) Attorney, Agent, or Firm—Fish & Neave; Joel Weiss; Jeffrey C. Aldridge

(57) ABSTRACT

Systems and methods for promoting ischemic preconditioning in individuals are provided. Ischemic preconditioning is provided by exercise treatments. The exercise treatments consist of breathing exercise regimens with breathing sequences of oxygenating and non-oxygenating phases co-ordinated with stress-relaxation cycles. The breathing sequences are designed to induce periods of ischemia. The individualized exercise treatments can induce optimal number of periods of ischemia separated by suitable intervals to provide effective ischemic preconditioning.

30 Claims, 7 Drawing Sheets

Heart Rate

Oxygenating

Non-Oxygenating

Blood Oxygen Saturation Level

SYSTEMS AND METHODS FOR BREATHING EXERCISE REGIMENS TO PROMOTE ISCHEMIC PRECONDITIONING

FIELD OF THE INVENTION

The present invention relates to systems and methods for promoting ischemic preconditioning in individuals. More particularly, the present invention relates to systems and methods for promoting ischemic preconditioning in individuals by exercise treatments that coordinate a breathing regimen with cycles of alternating stress and relaxation.

BACKGROUND OF THE INVENTION

Ischemic preconditioning is one of the most remarkable phenomena known to medical science. Brief periods of ischemia—a local shortage of oxygen-carrying blood supply, in biological tissue, renders that tissue more resistant to subsequent ischemic insults.

Ischemic preconditioning has been observed in myocardial tissue of dogs who were pretreated by alternately clamping and unclamping coronary arteries to intermittently turn off the blood flow to the heart. Dogs who were treated with an optimal number of four cycles of five-minute coronary occlusion followed by five-minute reperfusion, exhibited 75% smaller infarct sizes resulting from a subsequent forty-minute coronary occlusion. Fewer than four cycles of coronary occlusion resulted in insufficient preconditioning, more than four cycles did not provide further benefit.

Myocardial tolerance also develops in response to treatment that does not include coronary occlusion (i.e., ischemia) but increases demand for oxygenated blood. In dogs, a treatment comprising of five five-minute periods of tachycardia alternating with five minutes of recovery has been shown to reduce infarct sizes.

The myocardial resistance to infarct resulting from brief periods of ischemia has also been described in other animal species including rabbit, rat and pig. Ischemic preconditioning has also been demonstrated in humans. A second coronary occlusion during the course of coronary angioplasty often results in less myocardial damage than the first. Naturally occurring ischemic preconditioning of the myocardium has been found in humans suffering from bouts of angina.

Ischemic preconditioning occurs not only in myocardial tissue but also occurs in non-cardiac tissue including kidney, brain, skeletal-muscle, lung, liver and skeletal tissue. Further myocardial resistance to infarct exists even in virgin myocardium tissue following brief ischemia in spatially remote cardiac or non-cardiac tissue. Ischemic preconditioning also exhibits a temporal reach: An early phase develops immediately within minutes of the preconditioning ischemic injury and lasts for a few hours, and a late phase develops with circadian regularity twenty four hours later and reappears cyclically over several days, and then dissipates.

The spatial and temporal characteristics of ischemic preconditioning may be a manifestation of complex interactions between various underlying phenomena that are internal as well as external to the human body. However, the biochemical and cellular mechanisms underlying the phenomena of ischemic preconditioning are not yet fully understood despite several research efforts. These research efforts have been motivated at least in part by the hope of developing pharmaceutical drugs which would provide the anti-infarct effect of ischemic preconditioning. Though ischemic preconditioning in a bottle may be desirable, it is as of now a chimera.

In contrast to a pharmacological approach to medicine, a general non-pharmacological approach to improving an individual's physiological condition is based on physical exercise. Dardik, U.S. Pat. Nos. 5,007,430, 5,800,737, 5,163,439, and 5,752,521, and Dardik, U.S. patent application Ser. No. 09/609,087, which are hereby incorporated by reference in their entireties, elaborate on non-pharmacological exercise treatments. The exercise treatments described in Dardik are based on a perspective view of human physiology that recognizes the wave nature of cardiac activity. For example, cardiac activity manifests itself through repetitive pulsations of the heart as a heart wave. The heart wave is a result of a superposition of many underlying waves (i.e., cycles) including behavioral waves (e.g., energy expenditure and recovery cycles in response to physical activity), environmental waves (e.g., day-night cycles), and internal waves (e.g., molecular biological, cellular, and chemical cycles). The exercise treatments described by Dardik may target specific heart wave properties to enhance an individual's overall physiological condition. For example, the treatments seek to beneficially increase heart rate variability.

However, neither of these exercise treatments nor any other in the prior art directly target ischemic preconditioning, for example, for improved myocardial behavior.

It is desirable to have systems and methods for promoting ischemic preconditioning in individuals. Recognition of cardiac activity as wave phenomenon that results from a superimposition of the effects of various endogenous and exogenous phenomena on human physiology is consistent with an empirical understanding of the spatial and temporal characteristics of ischemic preconditioning. This recognition may enable non-pharmacological treatments that provide individuals with protective powers of ischemic preconditioning for both prophylaxis and therapy.

SUMMARY AND OBJECTS OF THE INVENTION

It is an object of the present invention to provide systems and methods for providing ischemic preconditioning in individuals.

It is a further object of the present invention to provide non-pharmacological and non-invasive treatments with the goal of promoting ischemic preconditioning in individuals in order to enhance health, performance and longevity.

These and other objects of the invention are accomplished in accordance with the principles of the present invention by providing systems and methods for providing exercise treatments that can use individualized breathing exercise regimens for promoting ischemic preconditioning. The exercise regimens can include one or more exercise sessions. Each session can consist of breathing sequences co-ordinated with one or more stress-relaxation cycles. The breathing sequences can consist of one or more breathing cycles designed to induce at least one incidence of ischemia in the individual. The breathing cycles can be defined, for example, by defining time periods for inhalation, exhalation, holding breath, and not inhaling following exhalation. Each of these cycles may be defined with respect to changes in the heart rate and predetermined exercise regimens including stress-relaxation cycles.

The stress-relaxation cycles of the exercise regimens, in accordance with the present invention, can be based, for example, on therapeutic and bio-rhythmic feedback principles taught by Dardik, U.S. Pat. Nos. 5,007,430, 5,800,737, 5,163,439, and 5,752,521, and Dardik, U.S. patent application Ser. No. 09/609,087. The stress-relaxation cycles can consist of one or more cycles, during which the individual attempts to increase his or her heart rate, for example, to a target heart rate.

The periods of stress in the stress-relaxation cycles correspond to periods of high metabolic demand for oxygen in the individual's body tissues. The breathing sequences of the exercise regimens, in accordance with the present invention, can include one or more breathing cycles that control the time periods during which the individual's blood is oxygenated. By coordinating periods of oxygenation and non-oxygenation with periods of high metabolic demand, the breathing sequences can cause a sufficient degree of oxygen deprivation in the body tissues to cause ischemia. The timing and duration of non-oxygenating phases can be designed to control the intensity and duration of oxygen deprivation to produce ischemia in specific body tissue types such as myocardial, lung, skeletal-muscle, brain, and muscle tissues, etc., and any combination thereof.

One or more incidents of ischemia can be repeated at suitable intervals in one or more exercise sessions to provide optimal ischemic preconditioning.

The breathing exercise regimens can be synchronized with endogenous and exogenous cyclical phenomena in accordance with this invention by application of the principles for therapeutic treatment taught by Dardik, U.S. Pat. No. 5,800,737. For example, the breathing exercise treatments may be synchronized with circadian waves to provide ischemic preconditioning at periods later than the ischemic incidents themselves.

The breathing exercise regimens can also be designed to provide non-ischemic myocardial tolerance by increasing oxygen demand. Oxygen demand can be increased by sequences of rapid deep breathing cycles that substantially increase the individual's heart rate. Alternatively, oxygen can be increased or decreased by respectively increasing or decreasing the oxygen content of the subject's environment. Changes in the oxygen content may be performed in a preferably pre-determined cyclical fashion. A system for cycling the oxygen environment of an individual may, for example, be a hypo/hyper baric chamber. Such a chamber should preferably include the capacity to increase or decrease the oxygen content of the atmosphere within the chamber.

According to one embodiment of the present invention, an exercise treatment for promoting ischemic preconditioning can be conducted using an apparatus to monitor and analyze physiological parameters. The analysis of physiological parameters can be used to provide individualized breathing exercise regimens to promote ischemic preconditioning. The exercise treatment can include one or more exercise sessions. In the exercise sessions, the individual can be subject to one or more stress-relaxation cycles during which metabolic demand for oxygen in body tissues increases. A physiological parameter such as blood oxygen saturation level that is indicative of ischemia, i.e., oxygen deprivation, in body tissue may be monitored during a stress-relaxation cycle. A time trace of parameter data is recorded in an electronic file. Then, the time trace is analyzed, for example, to assess parameter values relative to ischemic thresholds. The analysis can determine breathing cycle parameters and stress-relaxation cycle parameters that can cause ischemic incidents. These parameters can then be used to co-ordinate breathing sequences with one or more stress-relaxation cycles to generate individualized breathing exercise regimens that promote ischemic preconditioning.

According to another aspect of this invention, electronic networks, such as the Internet, can be used to receive data and provide information to the individual remotely.

BRIEF DESCRIPTION OF THE DRAWINGS AND THE APPENDIX

The above and other objects and advantages of the present invention will be apparent upon consideration of the following detailed description, taken in conjunction with the accompanying drawings, in which like reference characters refer to like parts throughout, and in which.

DETAILED DESCRIPTION OF THE INVENTION

In order that the invention herein described can be fully understood, the following detailed description is set forth.

Figure 1:
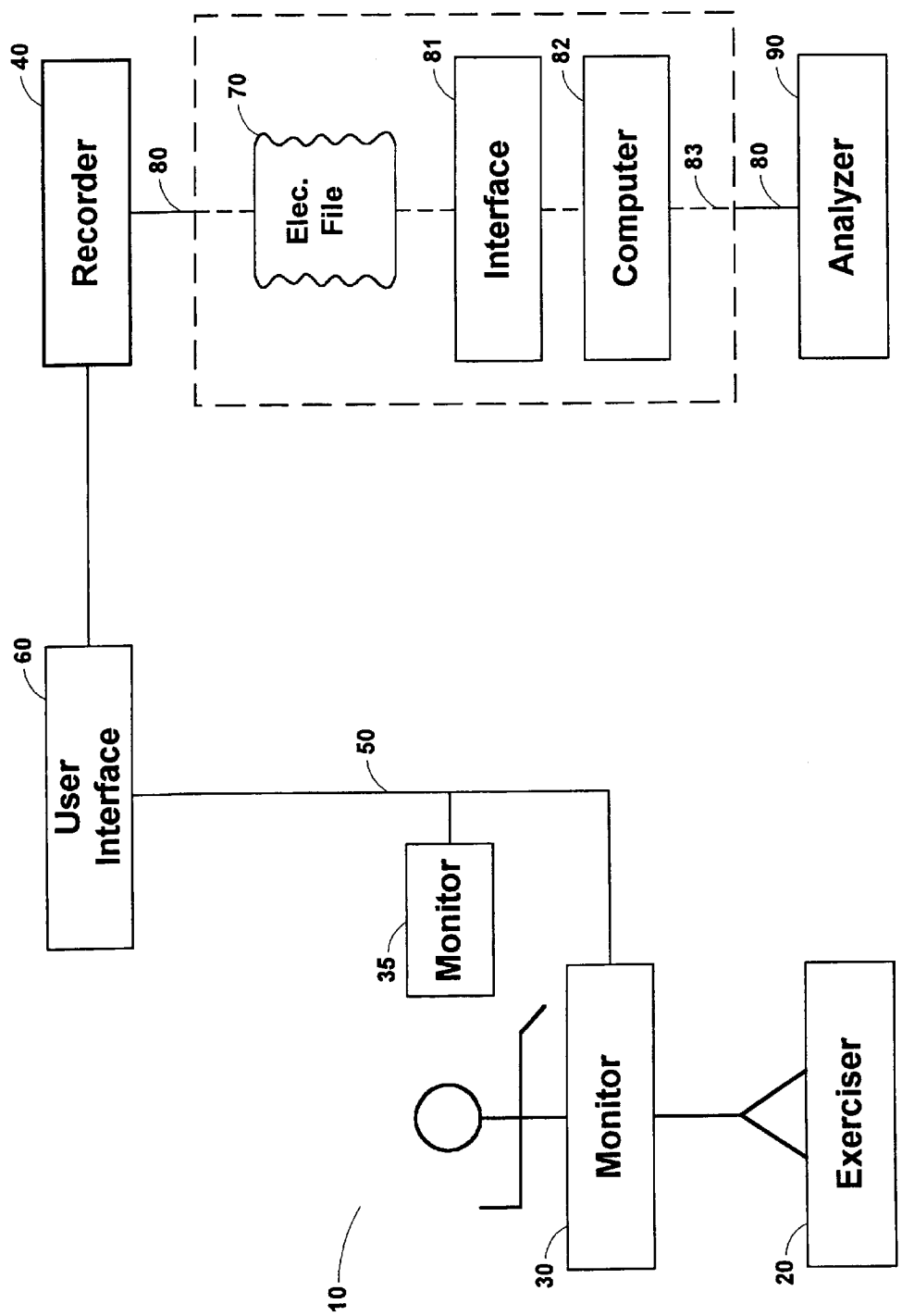
FIG. 1 is a schematic block diagram of an illustrative system constructed in accordance with the present invention.

FIG. 1 shows illustrative systems for exercise by an individual during performance of a breathing exercise regimen. One purpose of the systems is to incorporate ischemic preconditioning in the exercise.

Individual 10 is shown exercising on exerciser 20. Exerciser 20, for example, can be a treadmill machine, a trampoline, a stationary bicycle, or any other suitable exercising apparatus. Exerciser 20, however, is optional because exercise can be done without the aid of an exercise apparatus (e.g., running, jogging, jumping, walking, swimming, moving arms and shoulders, or swinging legs). Exercise may even be anaerobic activity. Monitor 35 monitors a physiological parameter indicative of the degree of ischemia. Physiological parameters which are indicative of ischemia are, for example, blood oxygen saturation levels, and in vivo concentrations of biochemical compounds such as protein kinase C, nitric oxide, and antioxidant enzymes including superoxide dismutase, catalese, gluthathione peroxidase, etc. Electronic monitor 30 may monitor other physiological parameters such as heart rate, heart rate variation, heart wave shape, blood pressure, and body temperature of individual 10. Even though two monitors 30 and 35 are shown, it must be understood that any monitoring including the number of monitors used is optional. Monitors 30 and 35 are optional, because routine exercise sessions may be conducted without any monitoring in accordance with the present invention.

Monitors 30 and 35 can be any commercially available units that measure blood oxygen saturation levels and heart rates, respectively, and transmits data to recorder 40 through link 50. Link 50 can be, for example, a magnetic coupling, a wireless transmission system, or any other electronic or electromagnetic network. Monitor 30 and 35 can be connected through link 50 to user interface 60. Interface 60 can include passive output devices that provide to users visual, auditory, or tactile information regarding the blood oxygen saturation level, the heart rate or any other type of data. Interface 60 can also include an active output device such as a breathing machine, a respirator, a heart-lung machine, and any combination thereof. Recorder 40 can be, for example, a printer, a chart recorder, or other device (or combination of devices) that can record a time trace of data in an electronic file 70.

Monitors 30, recorder 40, link 50, and interface 60 can be obtained commercially as an integrated heart monitoring and recording unit (such as Lifewave Personal Coach™, by Lifewaves International Inc., of Califon, N.J.). Monitor 35 may also be connected to recorder 40, through link 50 and interface 60 or otherwise. Link 80 connects recorder 40 to analyzer 90, and can be local or remote to exerciser 20. According to one embodiment, and as shown in FIG. 1, link 80 can include watch reading interface 81 (such as "Polar Advantage Interface System" Model 900622K sold under the under the trademark POLAR™, by Polar Electro Inc. of Woodbury, N.Y.), personal computer 82, and Internet link 83. It will be appreciated, however, that link 80 can be any electronic network that couples recorder 40 to analyzer 90 for data communication.

Analyzer 90 can include one or more electronic computing devices, preferably programmable computing devices (such as Model HP-VEE sold by Hewlett Packard Company, of Palo Alto, Calif.). It will be appreciated that analysis could, in some cases, exclusively or additionally involve manual computation or review, in accordance with the present invention. Analyzer 90 analyzes electronic file 70, which contains physiological data (e.g., blood oxygen saturation level data) to calculate individualized breathing exercise regimens for promoting ischemic preconditioning.

The exercises can include one or more exercise sessions. Each session comprises breathing sequences coordinated with one or more one stress-relaxation cycles. The breathing sequences can consist of one or more breathing cycles designed to induce at least one incidence of ischemia in the individual. Exercise regimens generated by analyzer 90 can be provided to individual 10, for example, over interface 60 or by any suitable means. Optionally, exercise regimens generated by analyzer 90 can be used to preprogram exerciser 20.

Figure 2:
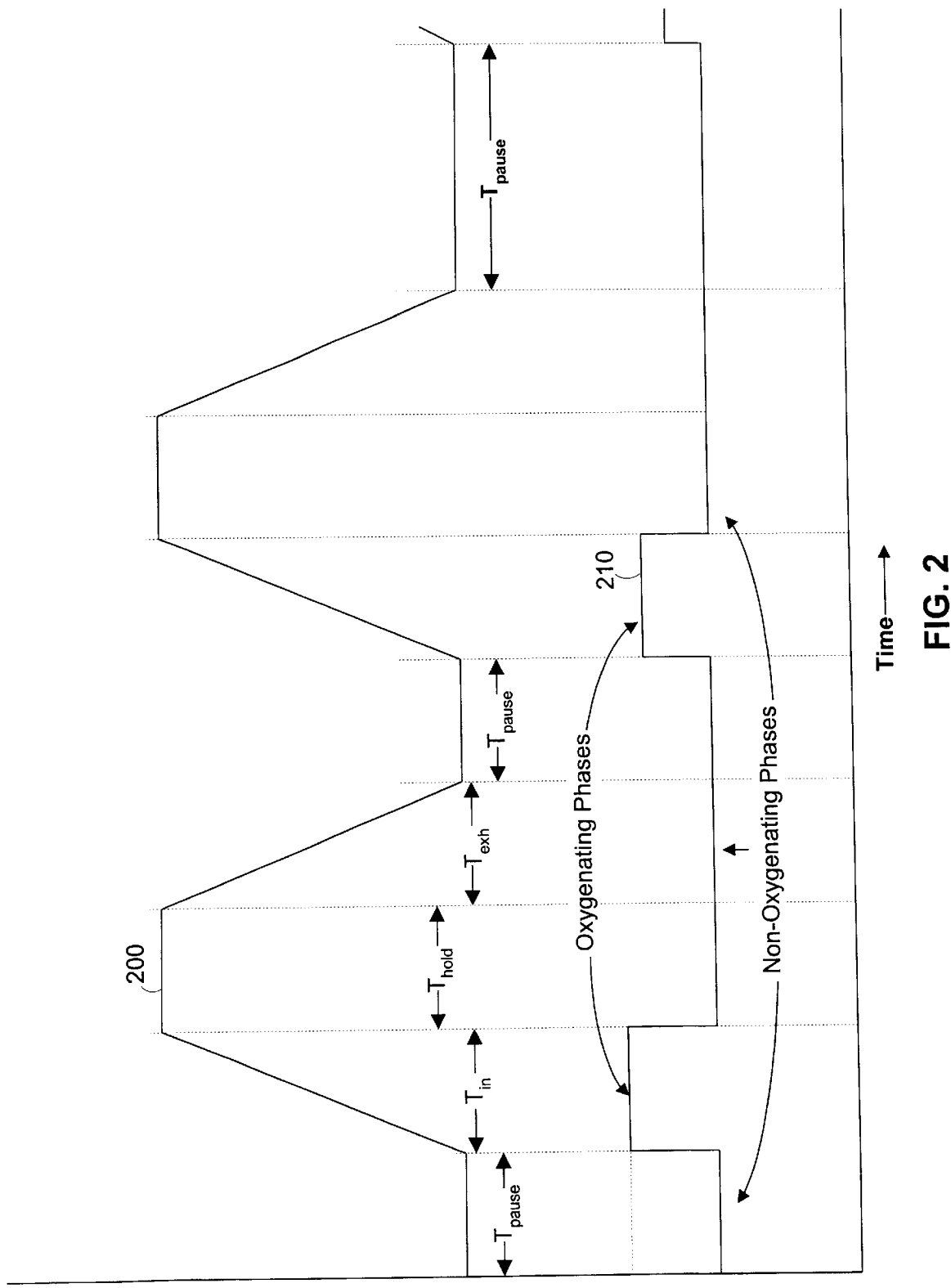
FIG. 2 is an illustrative sequence of breathing cycles and a time trace of corresponding oxygenating and non-oxygenating phases in accordance with the present invention.

FIG. 2 illustrates sequence of breathing cycles 200. Each breathing cycle in sequence 200 consists of an inhalation phase of duration $T_{in}$ that can be followed by an exhalation phase of duration $T_{exh}$. An optional holding phase of duration $T_{hold}$ can separate the inhalation and exhalation phase. Each breathing cycle may also include an optional pause phase of duration $T_{pause}$ separating it from a subsequent breathing cycle. Only during the inhalation phase of duration $T_{in}$ is blood oxygenated, as illustrated by trace 210.

Figure 3:
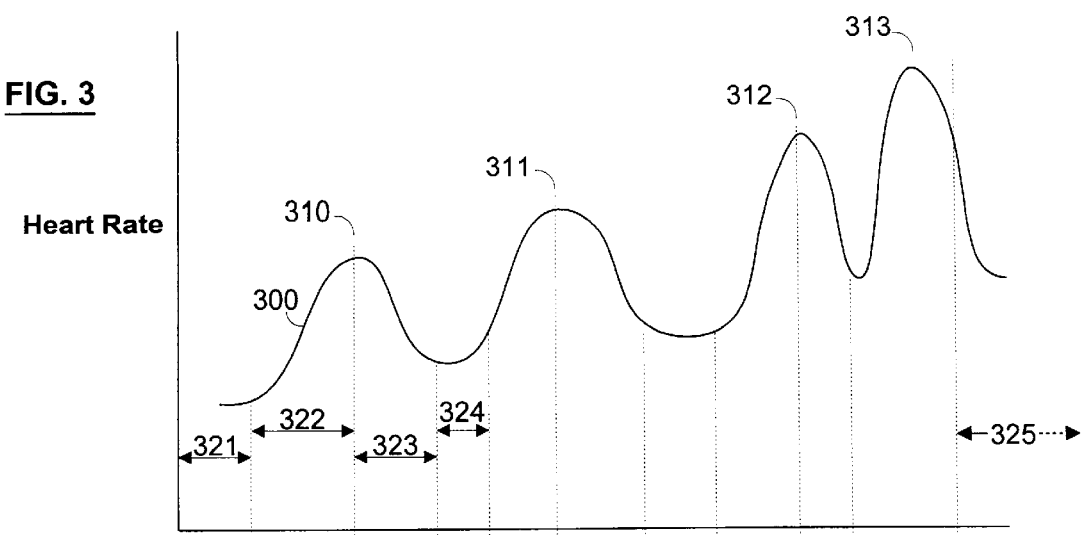
FIG. 3 is an illustrative time trace of heart rate data collected over several stress-relaxation cycles in an exercise session, in accordance with the present invention.
Figure 4:
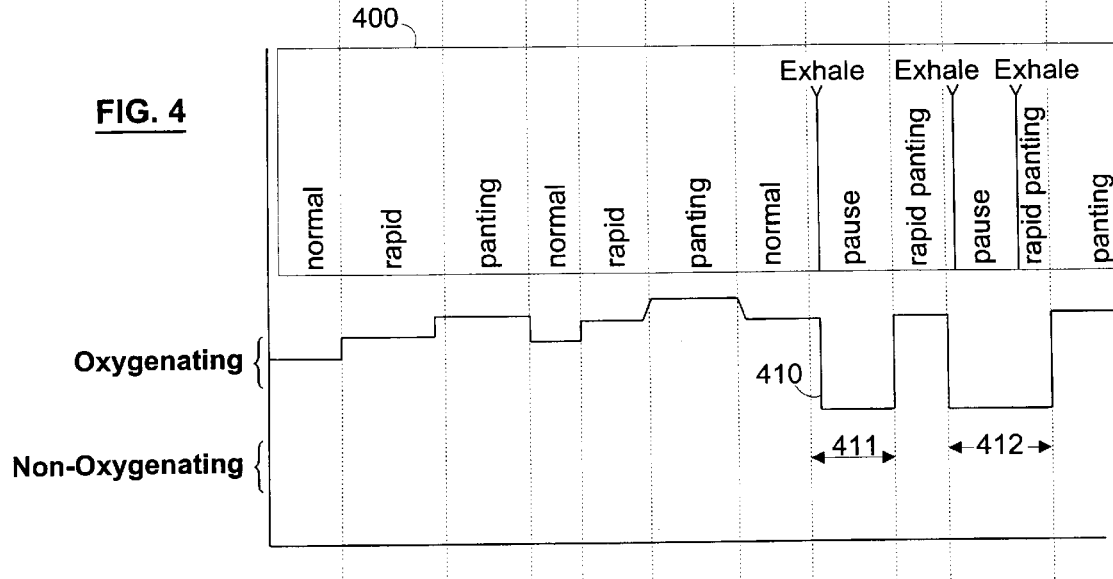
FIG. 4 shows an illustrative breathing regimen synchronized with the stress-relaxation cycles of the exercise session of FIG. 3, and a time trace of corresponding oxygenating and non-oxygenating phases, in accordance with the present invention.

FIG. 3 shows illustrative time trace 300 of an individual's heart rate while exercising according to a breathing exercise treatment session which, for example, consists of four successive stress-relaxation cycles 310–313. Some or all of cycles 310–313 can have designated target heart rates that an individual tries to attain during the cycle. Even though four cycles are shown for purposes of illustration, the number of stress-relaxation cycles in an exercise session can be as few as one at one end and at the other end can be limited only by what is physically possible, in accordance with the present invention. Breathing regimen 400 represented by "oxygenation and non-oxygenation" trace 410 in FIG. 4 is co-ordinated with stress-relaxation cycles 310–313.

In each of exercise cycles 310–313, the individual commences physical activity or exertion and continues the activity over first stress time period 322 in an attempt to raise the heart rate, for example, to a target heart rate. In each cycle 310–313, after stress period 322, the individual relaxes during relaxation time period 323 by gradually diminishing, or preferably, by abruptly ceasing physical activity. The exercise session can include pre-exercise rest period 321, intervening rest periods 324 between successive exercise cycles 310–313, and post-exercise resting period 325. During the exercise session through each of cycles 310–313 for each of periods 321, 322, 323, 324, and 325 the individual is expected to breath according to breathing regimen 400.

For cycles 310 and 311, breathing regimen 400 can call on the individual to regulated his oxygen intake by breathing at a normal (resting) rate during periods 321, a rapid rate during periods 322, and at a panting rate through periods 323. It will be appreciated that breathing regimen 400 can instruct the individual in general terms on the frequency and depth of breathing cycles for the normal, rapid, or the panting rates without specifically instructing the individual on breathing cycle parameters such as $T_{in}$, $T_{exh}$, $T_{hold}$, and $T_{pause}$, in accordance with the present invention.

Every single breathing cycle (as illustrated in FIG. 2) comprises an oxygenating phase and a non-oxygenating phase. However, in trace 310, for ease of illustration, entire periods of normal, rapid or panting breathing that can consist of several single breathing cycles are shown as single oxygenating phases.

For later exercise cycles 312 and 313 which can correspond to higher target heart rates than the first two cycles, breathing regimen 400 calls upon the individual to exhale and then pause breathing during all of increasing stress periods 322 (cycles 312 and 313) and also during all or portions of relaxation period 323 of cycles 313 (i.e., for cycle 312 $T_{exh}+T_{pause}{\approx}$period 322, and for cycle 313 $T_{exh}+T_{pause}{\approx}$period 322+period 323). These extended pauses in breathing are represented by non-oxygenating phases 411 and 412 in trace 410.

In FIG. 4 exhalation and pause durations $T_{exh}$ and $T_{pause}$ are shown for purposes of illustration as being comparable to periods 322 (and period 323). However, the time duration ($T_{exh}+T_{pause}$) corresponding to non-oxygenating phases in a breathing cycle can be larger or smaller than stress period 322 and/or relaxation period 323, in accordance with the present invention. For example, a breathing sequence may call on the individual to exhale and pause breathing only through a top portion of a stress period that corresponds to high stress, or may call on the individual to pause breathing throughout stress period 322.

Figure 5:
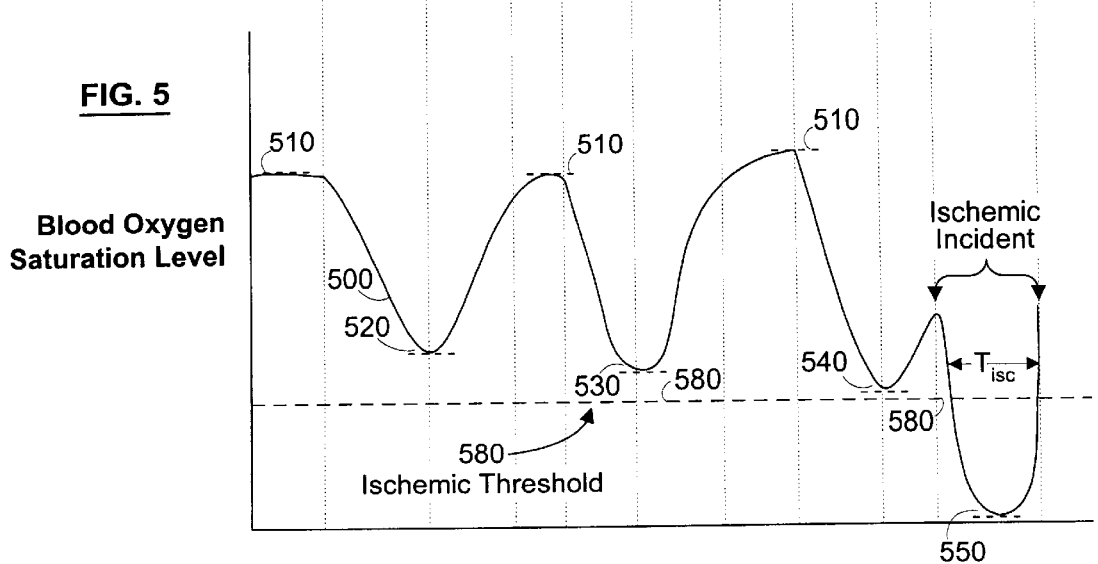
FIG. 5 shows a time trace of blood oxygen saturation levels corresponding to the exercise session of FIG. 3 in accordance with the present invention.

FIG. 5 shows illustrative time trace 500 of the individual's blood oxygen saturation level corresponding to heart rate time trace 300 and breathing regimen 400 as the individual is exercising and breathing according to breathing regimen 400. It will be understood that the blood oxygen levels shown in FIG. 5 are not clinically measured levels but are figurative levels used for purposes of illustration only.

First, considering exercise cycles 310 and 311, the individual's blood oxygen level is at resting level 510 during pre-exercise resting period 321, with blood oxygen levels maintained by normal (resting) breathing. Metabolic demand for oxygen in the individual's body tissues increases during periods of increasing stress (e.g., periods 322). In a normal physiological auto-response the individual may attempt to redress the imbalance between oxygen supply and demand by breathing more rapidly to replenish blood oxygen. However, at sufficiently increased stress, metabolic demand for oxygen in body tissues outpaces supply and blood oxygen saturation level drops to levels 520 and 530, for cycles 310 and 311, respectively. Nevertheless, repeated cyclical ischemic preconditioning can mitigate the reduction in blood oxygenation levels The drop in oxygen blood saturation level is an indication of the extent of oxygen deprivation and of a resulting "oxygen debt" owed to body tissue with high metabolic activity that has been under-supplied with oxygen. The degree of the oxygen debt or deprivation depends on the intensity and duration of total stress in relation to the level of blood oxygenation. Ischemia in a given type of body tissue (e.g., myocardium, lung tissue, skeletal-muscle tissue, etc.) can correspond to blood oxygen saturation levels below a certain threshold level $I_{threshold}$ which depends on the type of the tissue. The oxygen debt created by high metabolic demand can naturally cause the individual to breathe more deeply and more rapidly (e.g., by panting) in an attempt to restore blood oxygen saturation levels even as demand for oxygen decreases during relaxation periods (e.g., periods 323). Blood saturation levels may recover during the periods of rest (e.g., periods 324 and 325) accompanied by a return to normal (resting) breathing rates.

Now considering cycles 312 and 313, both cycles as illustrated in FIG. 3 have higher peak heart rates than earlier cycles 310 and 312. Thus, metabolic demand for oxygen is likely to be higher during cycles 312 and 313 than for earlier cycles 310 and 311. Further, breathing regimen 400 by requiring the individual to pause breathing (for duration $T_{pause}$) during the stress portion of cycle 312 (and also for the stress portion of cycle 313) prevents re-oxygenation of the blood during the periods of increased metabolic demand. As shown in FIG. 5 blood oxygen saturation levels drop to levels 540 and 550 for cycles 312 and 313, respectively. Ischemia results when blood oxygen saturation levels drops below ischemic threshold 580 (e.g., $I_{threshold}$(myocardium)). For example, level 550 corresponding to cycle 313 is below threshold 580. Rapid panting may be naturally induced or encouraged by the severe lack of oxygen that is represented by levels 540 and 550. Periods 413 shown in FIG. 4 indicate rapid panting caused by severe lack of oxygen. The ischemia persists for a duration $T_{isc}$ until renewed breathing coupled with reduced metabolic demand in period 325 restores the blood oxygen saturation level to values above threshold 580.

One ischemic "incident" is shown for purposes of illustration in FIG. 5. Optimal ischemic preconditioning can require one or more such ischemic incidents separated by suitable time intervals. By analyzing the individual's physiological parameters, breathing exercise regimens can be individually tailored to provide an optimal number of ischemic incidents of specific duration $T_{isc}$ separated by suitable time intervals to provide optimal ischemic preconditioning without tissue damage or necrosis. The breathing cycle parameters such as $T_{in}$, $T_{hold}$, $T_{exh}$, and $T_{pause}$, and stress-relaxation cycle parameters such as period 322 and target heart rates can be tailored to provide ischemic incidents of sufficient intensity and duration to generate biochemical and cellular chemistries that promote ischemic preconditioning. Additionally, the ischemic incidents can correspond to ischemic thresholds that correspond to specific tissues such as myocardial tissue, brain tissue, lung tissue, kidney tissue, skeletal-muscle, etc., and any combination thereof.

Figure 6:
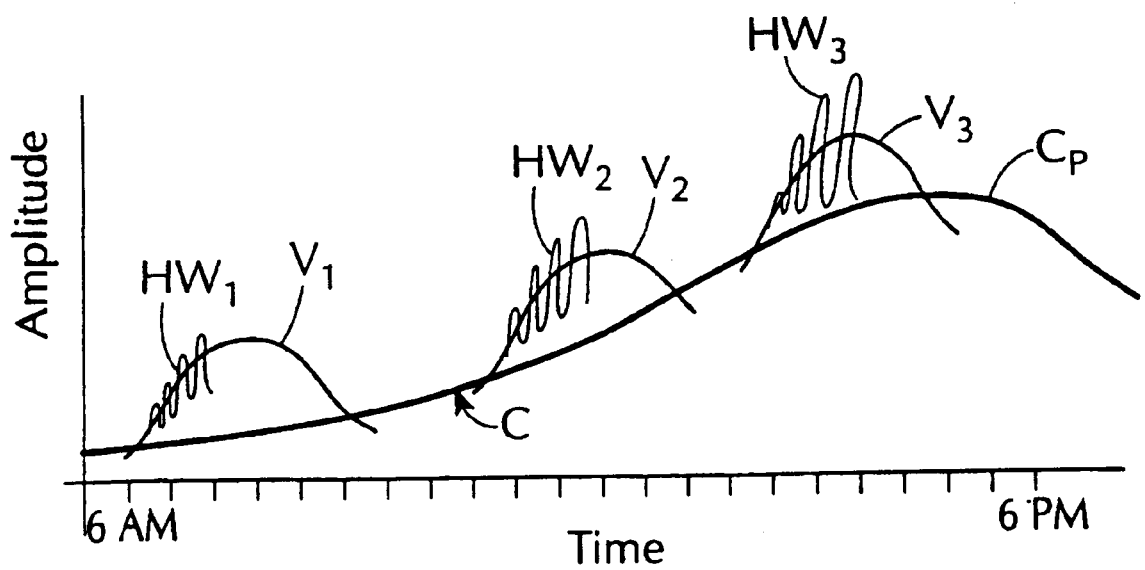
FIG. 6 illustrates the relationship between heart waves generated during exercise sessions and exogenous phenomena such as circadian waves and ultradian waves, in accordance with present invention.

The traces of FIGS. 3, 4, and 5 are shown for purposes of illustration as if the physiological responses to exercise stress-relaxation cycles occur in isolation of other physiological phenomena. It will be appreciated, however, that in reality several exogenous and endogenous phenomena are superimposed. The total stress endured by an individual represents superimposed stress due a variety of sources, for example, aerobic physical activity, anaerobic physical activity, heart wave activity, internal body functions, body temperature, blood pressure, and internal circadian wave activity. FIG. 6 shows, for example, a circadian heart wave plotted on a time scale, the circadian wave C rising in amplitude to a peak Cp at about 6:00 p.m. Between 6:00 a.m. and 6:00 p.m. three ultradian waves V1, V2, and V3 are produced, the first taking place early in the morning, the second in the late morning, and the third in the afternoon.

In FIG. 6 heart waves generated during three exercise sessions (similar to that illustrated in FIG. 2) are shown superimposed as HW1, HW2, and HW3. The exercise regimens of the present invention can account for the total varying stress levels in generating, for example, stress-relaxation cycle parameters such as period 322 and target heart rates for optimal ischemic preconditioning. It should be noted that the temperature of the environment in which a subject is exercising may be adjusted to increase or decrease the amplitude and/or frequency of the heart waves.

Further, as described in Dardik, U.S. Pat. No. 5,810,737, the three illustrated exercise sessions HW1, HW2, and HW3 are synchronized with the ultradian waves and circadian waves to optimize the beneficial effect of cyclical exercise techniques. Similarly, the breathing regimens of the present invention can be designed and synchronized with ultradian waves, circadian waves, and other cyclical endogenous or exogenous phenomena. The synchronization can enable biochemical and cellular chemistries resulting from ischemic incidents in an exercise session to entrain, for example, on circadian waves so that ischemic preconditioning can be effective at times later than the incidents themselves.

Another aspect of the present invention relates to obtaining the benefits of ischemic pre-conditioning without ischemia, such as non-ischemic myocardial tolerance that results from increased oxygen demand. Oxygenating phases corresponding to rapid or panting breathing rates (e.g., as shown in breathing regimen 400, FIG. 4) can be co-ordinated to correspond to periods of high oxygen demand in body tissue. In addition to increasing oxygen demand in body tissue by physical exercise, high oxygen demand can be triggered by the breathing regimen itself. For example, a deep breath causes an individual's heart rate to substantially fluctuate (indicating substantially increased and decreased demand for oxygen in the myocardium). Breathing exercise regimens may be individually tailored to provide a suitable number of high oxygen demand incidents (herein non-ischemic incidents) that increase myocardial tolerance.

Hereto, the present description illustrates the use of breathing exercise regimens to generate ischemic incidents and non-ischemic incidents separately. It will be appreciated, however, that in accordance with the present invention, the exercise treatments may consist of either one or both kinds of incidents. Either one or both kinds of incidents can be generated within an exercise session, for example, by using a breathing regimen that coordinates oxygenating phases with some periods of high oxygen demand to generate non-ischemic incidents, and co-ordinates non-oxygenating phases with other periods of high oxygen demand to generate ischemic incidents.

Methods of exercising according to the invention are also provided.

Figure 7:
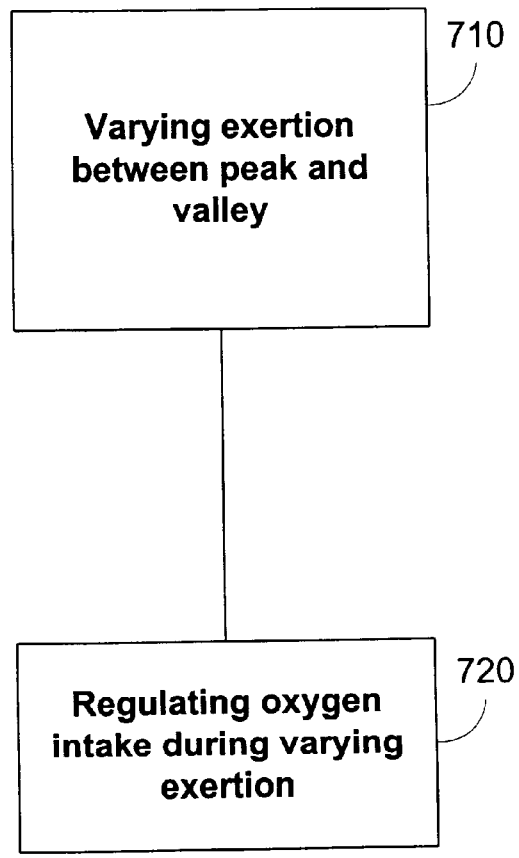
FIG. 7 is a flow chart of a preferred embodiment of a method in accordance with the present invention.

A preferred embodiment of a method according to the invention is shown by the flow chart 700 in FIG. 7. Box 710 shows a step of varying exertion during an exercise between a peak exertion (high) and a valley exertion (low). This varying creates an exercise program that increases heart rate variability and preferably substantially improves health.

Box 720 shows regulating the intake of oxygen during the varying. It should be noted that the regulating can be implemented at any point during the varying to obtain the benefits of the invention.

The regulating of the oxygen intake may include either depriving oxygen from the subject exercising or exaggerating his oxygen intake, e.g., by placing him in a relatively oxygen-rich environment.

This regulation may also be preferably implemented in periodic or cyclical fashion. In this way, waves are created in the heart function such that heart rate variability and other characteristics of the heart are improved.

The heart rate variability is improved because the cyclical regulation causes the myocardial oscillatory chemistry to swing up and down, thereby augmenting the heart rate variability already set in motion by the varying of the exertion shown in Box 710. The result of this is that the myocardium is substantially protected because of the heightened heart rate communication, organization and coherence of the waves in the heart.

Figure 8:
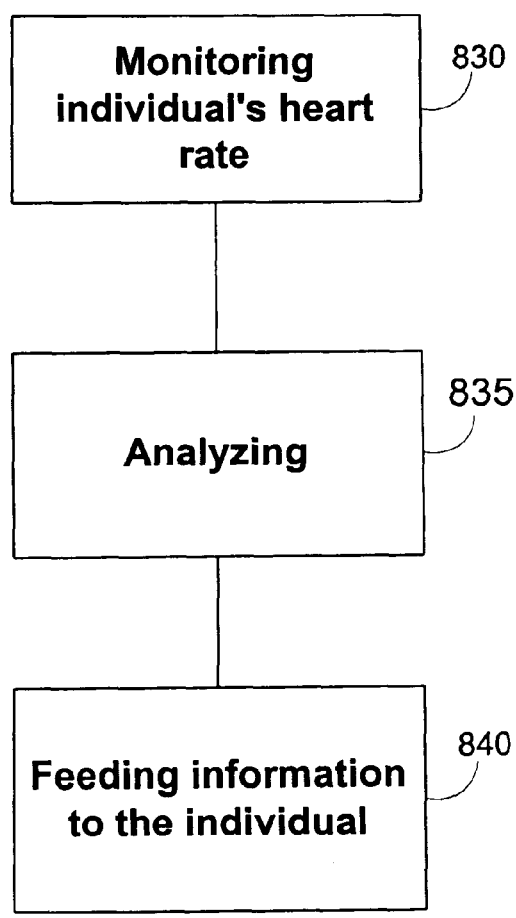
FIG. 8 is a flow chart showing further details of the method of FIG. 7, in accordance with the present invention.

FIG. 8 shows a more detailed flow chart of the method according to the invention. In this method, box 830 indicates a monitoring of the heart rate of an individual subject. Box 835 represents analyzing monitored data to determine breath regulation windows or sequences. Box 840 shows feeding back information in order to communicate the breath regulation windows to the subject. This may be accomplished through an audio or an audio/video feedback mechanism.

It is generally preferable to implement oxygen deprivation proximal to the end of an exercise session. Thus, in an exemplary exercise session(s), each session preferably including six cycles of variation in the heart rate, it may be preferable to regulate oxygen during a portion of the last two or three cycles. The length of the oxygen regulation depends on the health and endurance of the subject and should be determined with the aid of a knowledgeable professional.

Figure 9:
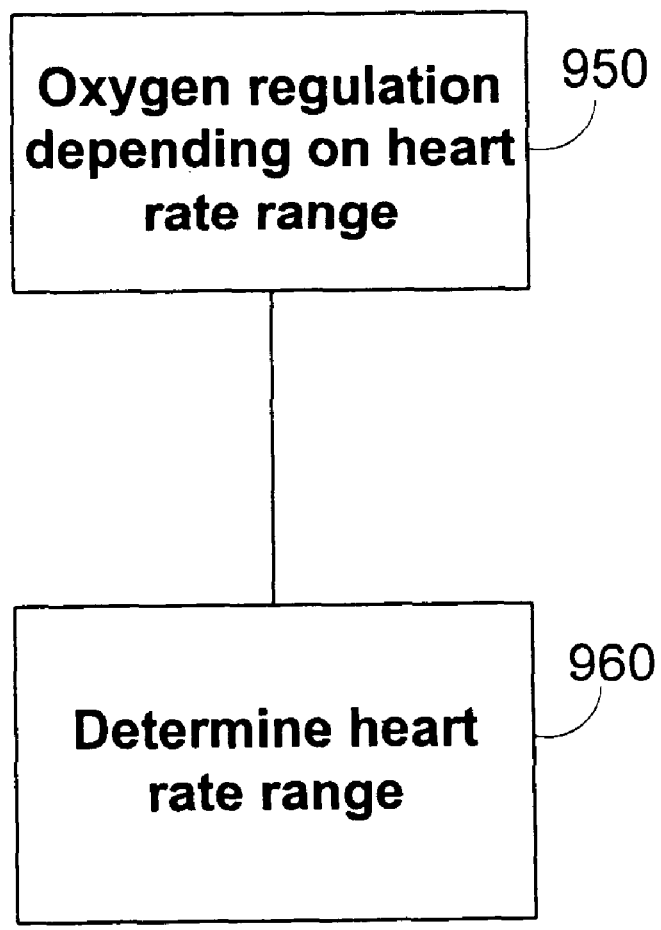
FIG. 9 is a flow chart of an alternative embodiment of a method in accordance with the present invention.

FIG. 9 shows an alternative embodiment of the invention wherein box 960 indicates that the oxygen regulation should preferably be implemented at different heart rate ranges (e.g., 100–120, 110–130, 120–140 beats/min, etc.) determined at box 950. This provides pre-conditioning to the heart across a range of heart rates. One possible advantage obtained by such a method includes pre-conditioning an athlete to have potentially advantageous cardiac characteristics across an entire range of heart rates. Therefore, when the athlete is performing at a high heart rate, he possesses a reservoir of positive cardiac response. This reservoir serves to help overcome the obstacles of high heart rate/extreme oxygen requirement intervals.

In yet another embodiment of the invention, the periodic oxygen regulation can be used with weight training. In this embodiment, the maximum strength output periods can be established by using oxygen regulation. For example, the oxygen regulation can be repeated in a particular time of the day, e.g., the late afternoon, such that a wave is created in the subject which provides maximum strength output in the period of the oxygen regulation, i.e., in the late afternoon.

As used herein, electronic networks could include a local area network, a wireless network, a wired network, a wide area network, the Internet, and any combination thereof. An electronic network can provide links to user interfaces (e.g., interface 60, FIG. 1) used for sending or receiving data. The interfaces can be any one or more of commercially available interface devices such as a web page, a web browser, a plug-in, a display monitor, a computer terminal, a modem, an audio device, a tactile device (e.g., vibrating surface, etc.), or any combination thereof.

In accordance with the present invention, software (i.e., instructions) for controlling the aforementioned apparatus can be provided on computer-readable media. It will be appreciated that each of the steps (described above in accordance with this invention), and any combination of these steps, can be implemented by computer program instructions. These computer program instructions can be loaded onto a computer or other programmable apparatus to produce a machine, such that the instructions which execute on the computer or other programmable apparatus create means for implementing the functions specified in the flowchart block or blocks. These computer program instructions can also be stored in a computer-readable memory that can direct a computer or other programmable apparatus to function in a particular manner, such that the instructions stored in the computer-readable memory produce an article of manufacture including instruction means which implement the function specified in the flowchart block or blocks. The computer program instructions can also be loaded onto a computer or other programmable apparatus to cause a series of operational steps to be performed on the computer or other programmable apparatus to produce a computer implemented process such that the instructions which execute on the computer or other programmable apparatus provide steps for implementing the functions specified in the flowchart block or blocks.

It will be understood that the foregoing is only illustrative of the principles of the invention, and that various modifications can be made by those skilled in the art without departing from the scope and spirit of the invention.

I claim:

1. An apparatus for providing an exercise treatment to promote ischemic preconditioning in an individual, said treatment using a breathing exercise regimen, said apparatus comprising:
   at least one monitor to monitor at least one physiological parameter indicative of ischemia;
   an analyzer coupled to said at least one monitor, wherein said analyzer analyzes said at least one parameter and generates said breathing exercise regimen that is designed to induce at least one period of ischemia; and
   an interface coupled to said analyzer, wherein said interface provides said breathing exercise regimen to said individual.

2. The apparatus of claim 1 wherein said at least one monitor monitors said at least one physiological parameter that is selected from a group consisting of a heart rate, a heart rate variability, a heart wave shape, a blood oxygen saturation level, a protein kinase C concentration, a nitric oxide concentration, and concentrations of antioxidant enzymes including superoxide dismutase, catalese, and gluthathione peroxidase.

3. The apparatus of claim 1 further comprising an exerciser operated by the individual to create said at least one stress-relaxation cycle.

4. The apparatus of claim 3 wherein said exerciser is preprogrammed with said exercise regimen generated by said analyzer.

5. The apparatus of claim 1 further comprising:
a first link for coupling said at least one monitor to said analyzer; and
a second link for coupling said analyzer to said interface, wherein said links are selected from the group consisting of a wireless communication system, a wired communication system, an electronic network, and any combination thereof.

6. The apparatus of claim 5 wherein said electronic network comprises a network selected from the group consisting of a local area network, a wide area network, an Intranet, an Internet and any combinations thereof.

7. The apparatus of claim 1 wherein said interface is a passive output device selected from the group consisting of a visual device, an auditory device, a tactile device, and any combination thereof.

8. The apparatus of claim 1 wherein said interface is an active output device selected from the group consisting of a breathing machine, a respirator, a heart-lung machine, and any combination thereof.

9. The apparatus of claim 1 wherein said analyzer generates said breathing regimen that promotes ischemic preconditioning of at least one type of body tissue selected from the group consisting of myocardial tissue, brain tissue, lung tissue, kidney tissue, skeletal, skeletal-muscle tissue, and any combination thereof.

10. The apparatus of claim 1 wherein said analyzer generates said exercise breathing regimen that comprises a sequence of at least one breathing cycle co-ordinated with at least one stress-relaxation cycle of a first duration, and wherein said at least one breathing cycle comprises at least one exhalation of a second duration, at least one inhalation of a third duration.

11. The apparatus of claim 10, wherein said analyzer generates said at least one breathing cycle that further comprises at least one pause of a fourth duration.

12. The apparatus of claim 11 wherein said analyzer generates said at least one breathing cycle such that said cycle is co-ordinated with said at least one stress-relaxation cycle to induce said at least one period of ischemia for a fifth duration.

13. The apparatus of claim 12 wherein said analyzer generates said breathing exercise regimen wherein said fifth duration depends on said first, second, third, and fourth durations and on a varying level of stress in said stress-relaxation cycle, and wherein said fifth duration is designed so that biochemical and cellular chemistries that promote ischemic preconditioning are produced during said ischemic period.

14. The apparatus of claim 13 wherein said varying level of stress represents superimposed stress due to at least one source that is selected from the group of sources consisting of aerobic physical activity, anaerobic physical activity, heart wave activity, internal body functions, internal circadian wave activity, and any combination thereof.

15. The apparatus of claim 14 wherein said individual has an internal circadian wave activity having a period, and wherein said analyzer generates said exercise breathing regimen that is synchronized with said circadian wave and such that said first, second, third, forth, and fifth durations are designed to cause said biochemical and cellular chemistries to entrain on said circadian wave so that said ischemic preconditioning is effective at later times that are multiples of said circadian period.

16. The apparatus of claim 11 wherein said analyzer generates said breathing regimen wherein first duration is greater than sum of said second and fourth durations.

17. The apparatus of claim 11 wherein said analyzer generates said breathing regimen wherein first duration is comparable to sum of said second and fourth durations.

18. The apparatus of claim 11 wherein said wherein said analyzer generates said breathing regimen wherein first duration is smaller than sum of said second and fourth durations.

19. The apparatus of claim 1 wherein said analyzer generates said breathing exercise regimen comprising:
at least one oxygenating phase of breathing states selected from the group consisting of an inhalation, a pause, a hold, and any combination thereof, said oxygenating phase corresponding to a first period during which blood is oxygenated; and
at least one non-oxygenating phase of breathing states selected from the group of states consisting of an exhalation, a pause, a hold, and any combination thereof, said non-oxygenating phase corresponding to a second period during which said which blood is not oxygenated.

20. The apparatus of claim 19 wherein said analyzer generates said breathing exercise regimen wherein during said at least one non-oxygenating phase said individual's blood oxygen saturation level decreases below an ischemic threshold.

21. The apparatus of claim 20 wherein said analyzer generates said breathing exercise regimen wherein said blood oxygen saturation level is below said threshold for said at least one period of ischemia.

22. The apparatus of claim 21 wherein said analyzer generates said breathing exercise regimen wherein said at least one ischemic period is designed to produce biochemical and cellular chemistries that promote ischemic preconditioning.

23. The apparatus of claim 21 wherein said analyzer generates said breathing exercise regimen wherein said at least one ischemic period is co-ordinated with said at least one stress-relaxation cycle.

24. The apparatus of claim 23 wherein said analyzer generates said breathing exercise regimen wherein said at least one ischemic period depends on a varying level of stress in said stress-relaxation cycle.

25. The apparatus of claim 24 wherein said varying level of stress represents superimposed stress due to at least one source that is selected from the group of sources consisting of aerobic physical activity, anaerobic physical activity, heart wave activity, internal body functions, internal circadian wave activity, and any combination thereof.

26. The apparatus of claim 25 wherein said individual has an internal circadian wave activity that has a period and wherein said analyzer generates said breathing exercise regimen with said at least one period of ischemia designed to cause said biochemical and cellular chemistries to entrain on said circadian wave so that said ischemic preconditioning is effective at later times that are multiples of said circadian period.

27. The apparatus of claim 21 wherein said analyzer generates said breathing exercise regimen wherein said at least one period of ischemia is greater than said first duration.

28. The apparatus of claim 21 wherein said analyzer generates said breathing exercise regimen wherein said at least one period of ischemia is comparable to said first duration.

29. The apparatus of claim 21 wherein said analyzer generates said breathing exercise regimen wherein said at least one period of ischemia is smaller to said first duration.

30. A kit comprising an apparatus for providing an exercise treatment according to a breathing exercise regimen to promote ischemic preconditioning in an individual, and a set of instructions for using said apparatus, wherein said apparatus comprises:

at least one monitor to monitor at least one physiological parameter indicative of ischemia;

an analyzer coupled to said at least one monitor, wherein said analyzer analyzes said at least one parameter and generates said breathing exercise regimen that is designed to induce at least one period of ischemia; and an interface coupled to said analyzer, wherein said interface provides said breathing exercise regimen to said individual; and wherein said set of instructions comprises:
at least one instruction on using said at least one monitor; and
at least one instruction on using said analyzer.

* * * * *